(12) United States Patent
Weems

(10) Patent No.: US 9,132,019 B2
(45) Date of Patent: Sep. 15, 2015

(54) METACARPAL-PHALANGEAL PROSTHESIS

(71) Applicant: Andrew C. Weems, Johnson City, TN (US)

(72) Inventor: Andrew C. Weems, Johnson City, TN (US)

(*) Notice: Subject to any disclaimer, the term of this patent is extended or adjusted under 35 U.S.C. 154(b) by 115 days.

(21) Appl. No.: 13/987,668

(22) Filed: Aug. 20, 2013

(65) Prior Publication Data

US 2014/0114428 A1 Apr. 24, 2014

Related U.S. Application Data

(60) Provisional application No. 61/795,647, filed on Oct. 22, 2012.

(51) Int. Cl.
*A61F 2/42* (2006.01)
*A61F 2/30* (2006.01)

(52) U.S. Cl.
CPC ............ *A61F 2/4241* (2013.01); *A61F 2/4225* (2013.01); *A61F 2002/3082* (2013.01); *A61F 2002/30327* (2013.01); *A61F 2002/4228* (2013.01); *A61F 2002/4233* (2013.01); *A61F 2002/4243* (2013.01); *A61F 2002/4251* (2013.01)

(58) Field of Classification Search
CPC ........... A61F 2/4241; A61F 2002/4243; A61F 2002/4251
USPC ............................................ 623/21.15, 21.16
See application file for complete search history.

(56) References Cited

U.S. PATENT DOCUMENTS

| | | |
|---|---|---|
| 3,462,765 A | 8/1969 | Swanson |
| 3,593,342 A | 7/1971 | Niebauer et al. |
| 3,638,243 A | 2/1972 | Campbell, Jr. et al. |
| 3,681,786 A | 8/1972 | Lynch |

(Continued)

FOREIGN PATENT DOCUMENTS

| | | |
|---|---|---|
| EP | 0 538 285 B1 | 4/1993 |
| WO | WO 97/12566 A1 | 10/1997 |

OTHER PUBLICATIONS

Pylios, T., "A New Metacarpophalangeal Joint Replacement Prosthesis", thesis for doctor degree in Philosophy, Biomedical Engineering Research Group School of Mechanical Engineering, University of Birmingham, Jan. 2010, (pp. 1-209) US.

*Primary Examiner* — David Isabella
*Assistant Examiner* — Dinah Baria
(74) *Attorney, Agent, or Firm* — Mark L. Davis

(57) ABSTRACT

A surgically implantable metacarpal-phalangeal prosthetic replacement device having engaging male and female components. The male and female components each include a conically shaped shank. The male head portion connected to the first conically shaped shank includes two spaced-apart lateral condyles having convex condylar surfaces and an intercondylar portion juxtaposed between the first and second convex condyles. The female component has a female head portion connected to the second conically shaped shank. The female head portion includes spaced-apart lateral side portions having concave recessed load-bearing surfaces that are complementary to and moveably engage the convex condylar surfaces of the male component. The lateral sides portions further define an intermediate concave condylar recess that moveably engages the outwardly extending intercondylar portion. The female head portion further includes substantially longitudinally aligned first and second protuberances which define a median channel portion for reception of the extensor tendons.

11 Claims, 4 Drawing Sheets

(56) References Cited

U.S. PATENT DOCUMENTS

| | | |
|---|---|---|
| 3,760,427 A | 9/1973 | Schultz |
| 3,869,729 A | 3/1975 | Attenborough |
| 3,946,445 A | 3/1976 | Bentley et al. |
| 3,991,425 A | 11/1976 | Martin et al. |
| 3,992,726 A | 11/1976 | Freeman et al. |
| 4,156,296 A | 5/1979 | Johnson et al. |
| 4,231,121 A | 11/1980 | Lewis |
| 4,242,759 A | 1/1981 | White |
| 4,642,122 A | 2/1987 | Steffee |
| 4,685,919 A | 8/1987 | Niwa et al. |
| 4,725,280 A | 2/1988 | Laure |
| 5,007,932 A | 4/1991 | Bekki et al. |
| 5,133,761 A | 7/1992 | Krouskop |
| 5,147,386 A | 9/1992 | Carignan et al. |
| 5,405,399 A | 4/1995 | Tornier |
| 5,405,401 A | 4/1995 | Lippincott, III et al. |
| 5,458,648 A * | 10/1995 | Berman et al. ............. 623/21.19 |
| 5,674,297 A | 10/1997 | Lane et al. |
| 6,159,247 A | 12/2000 | Klawitter et al. |
| 6,352,560 B1 | 3/2002 | Poeschmann et al. |
| 6,423,097 B2 | 7/2002 | Rauscher |
| 6,682,565 B1 | 1/2004 | Krishnan |
| 6,689,169 B2 * | 2/2004 | Harris ....................... 623/21.16 |
| 6,699,292 B2 | 3/2004 | Ogilvie et al. |
| 2008/0039949 A1 | 2/2008 | Messenburg et al. |

* cited by examiner

METACARPAL-PHALANGEAL PROSTHESIS

CROSS REFERENCE TO RELATED APPLICATIONS

This application is a non-provisional filing claiming benefit to the earlier filed provisional application having U.S. Ser. No. 61/795,647 filed Oct. 22, 2012, the entire disclosure of which is incorporated herein by reference.

BACKGROUND OF THE INVENTION

1. Field of the Invention

The present invention relates to surgically implantable prosthetic replacement devices for joints in the hand and toe. More particularly, the present invention is directed to interphalangeal and metacarpal-phalangeal joints that have been subjected damage due to externally applied forces, such as in an accident, and/or advanced diseases such as rheumatoid arthritis, ankylosis and the like.

2. Description of the Prior Art

The metacarpophalangeal joint is crucial for hand function. However, this joint is frequently affected by debilitating circumstances. The metacarpophalangeal joint is the articulation between the metacarpal and phalange bones in the hand and comprises a metacarpal head, the proximal phalanx, volar plate, two collateral ligaments, two accessory collateral ligaments and the sagittal band. A normal joint has the appearance of a ball-and-socket with three degrees of movement. Primarily motion is in the flexion, and extension direction, but is also capable of minor abduction and adduction rotation.

As can be seen, the metacarpophalangeal joint is complex. In recent years, surgically implantable prosthetic replacement devices have been developed to replace a damaged metacarpophalangeal joint, however, these devices have had varying degrees of success. An extensive medical literature has developed parallel to the patent literature in which numerous devices are described. There are a number of patents that specifically address various structures to replace the joints within the finger, particularly between the phalangeal bones of the hand.

Such devices can comprise single body construction or can be comprised of two or more articulating parts hinged or joined together in a variety of ways. One-piece prosthetic devices generally are composed of a flexible elastomer, such as silicone rubber, are described in U.S. Pat. Nos. 3,462,765; 3,593,342 and 3,681,786. These appear to be suitable as long as the integrity of the device is retained but may be subject to mechanical fatigue over time. Fracture problems have been reported in the medical literature. One problem with this type of prosthesis is that there is little or no lengthwise "play" or "give". This longitudinal rigidity can result in loosening the attachment of such devices to the bones.

Other devices utilize two or more components. For example, U.S. Pat. No. 4,156,296 discloses an endoprosthetic device for placement between metatarsal and phalangeal bones having a convex, part-spherical bearing surface having a projecting stem for securing the proximal component into the metatarsal. The distal portion of the device has a concave, part-spherical bearing surface with a projecting stem for securing the distal component into the end of the phalanx adjacent to the first metatarsal. The engagement of the two components forms a less-than-hemispherical articulation. Similar to this construction are devices disclosed in U.S. Pat. Nos. 4,231,121; 4,242,759; and 4,642,122 to identify but a few.

U.S. Pat. Nos. 5,133,761; 5,147,386; and 6,352,560 disclose multi-component finger joint prosthesis having a first part with a cylindrical socket and a second part with a cylindrical head. The cylindrical head and socket are of complementary form, in such a manner that together they are able to form a linear hinge. In the '761 and '560 patents, the cylindrical head is provided with a radial thickened section that extends in the circumferential direction. The cylindrical socket is provided with a radial recess extending circumferentially and which engages the radial thickened section in bearing contact inside the cylindrical socket. The radial thickened section and radial recess are arranged centrally and are formed so as to be self-aligning with respect to one another.

These synthetic joints do not always replicate the characteristics of a human phalangeal joint. As noted above, the human phalangeal joint has the ability to flex in one plane just as one may curl the finger. The human joint can endure lateral movement and slight twisting. Additionally, a form of longitudinal play is possible along the length of the phalangeal joint. These four degrees of motion have been difficult to achieve in a synthetic joint which is also durable, easily assembled, modular in approach so that an optimal bone-to-implant interface can be achieved, easily put into the human body, and which best replicates the joint that it replaces.

There is a great need in the prosthetic industry for phalangeal replacement joints, as well as other joints, which can achieve all of the desirable attributes articulated above. It is an object of this invention to provide a two part joint prosthesis having substantial freedom from mechanical fatigue and permitting small longitudinal hyperextension without loss of function.

SUMMARY OF THE INVENTION

Briefly, the present invention is a surgically implantable metacarpal-phalangeal prosthetic replacement device that replicates the various movements available in a human phalangeal or other joint. More specifically, the novel and inventive prosthesis provides for phalangeal joint replacement between proximal and distal phalangeal bones or between a distal phalangeal bone and a metacarpal bone and comprises two engaging components; for convenience of description the two components are termed and described as a male component and a female component. As is described in greater detail below, the identifying male component includes a semi-circular, outwardly extending portion or ridge that engages with a channel on the identifying female component. Either the male or the female component may be proximal under desired conditions of implantation, or alternatively either may be distal.

Each component includes (a) a tapered, conically shaped shank or pylon having a relatively smaller diameter terminal portion that is inserted into the medullary canal of a bone after a predetermined channel is created; and a relatively larger, distally spaced portion that adjoins or is adjacent to a (b) head portion. In a preferred embodiment the conically shaped shank or pylon includes a groove or channel that facilitates insertion of the pylon into the medullary canal.

The male head portion bears two spaced-apart lateral condyles each with a convex surface having a circular arc of greater than 180° around a center of curvature. Positioned substantially intermediately and substantially longitudinally aligned is an intercondylar portion extending outwardly relative to the convex surface of the juxtaposed condyles. The intercondylar portion substantially follows the curvature of the condyles convex shape and is adapted to engage a channel in the female head. The convex surface of each condyle acts as a load-bearing surface.

The female head portion includes two spaced-apart lateral sides having concave recessed load-bearing surfaces that are complementary to and adapted for movably engaging the convex surfaces of the condyles of the male component. The lateral sides define an engaging channel portion adapted to complementary interface with the outwardly extending intercondylar portion of the male component with an intercondylar fit or tolerance of up to about 0.2 mm.

The upper or dorsal surface of the female head portion includes spaced-apart, substantially longitudinally oriented protuberances which define a channel, trough, or groove which is adapted to receive the appropriate extensor tendon which together with retained ligaments and flexor tendons serve to hold the two portions of the prosthesis in alignment. Excessive hyperextension can result in dislocation or subluxation but resetting should be possible as with any normal joint that is dislocated by hyperextension.

It is an object of the present invention to provide a surgically implantable prosthetic replacement device for joints in the hand and toe.

Another object of the present invention is to provide a surgically implantable prosthetic replacement device for interphalangeal and metacarpal-phalangeal joints.

These and other objects and advantages of the present invention will become more apparent to those skilled in the art in view of the following description and the accompanying drawings wherein like parts and objects in the several views have similar reference numerals. It is to be understood that the inventive concept is not to be considered limited to the constructions disclosed herein but instead by the scope of the appended claims.

DETAILED DESCRIPTION OF THE INVENTION

Figure 1:
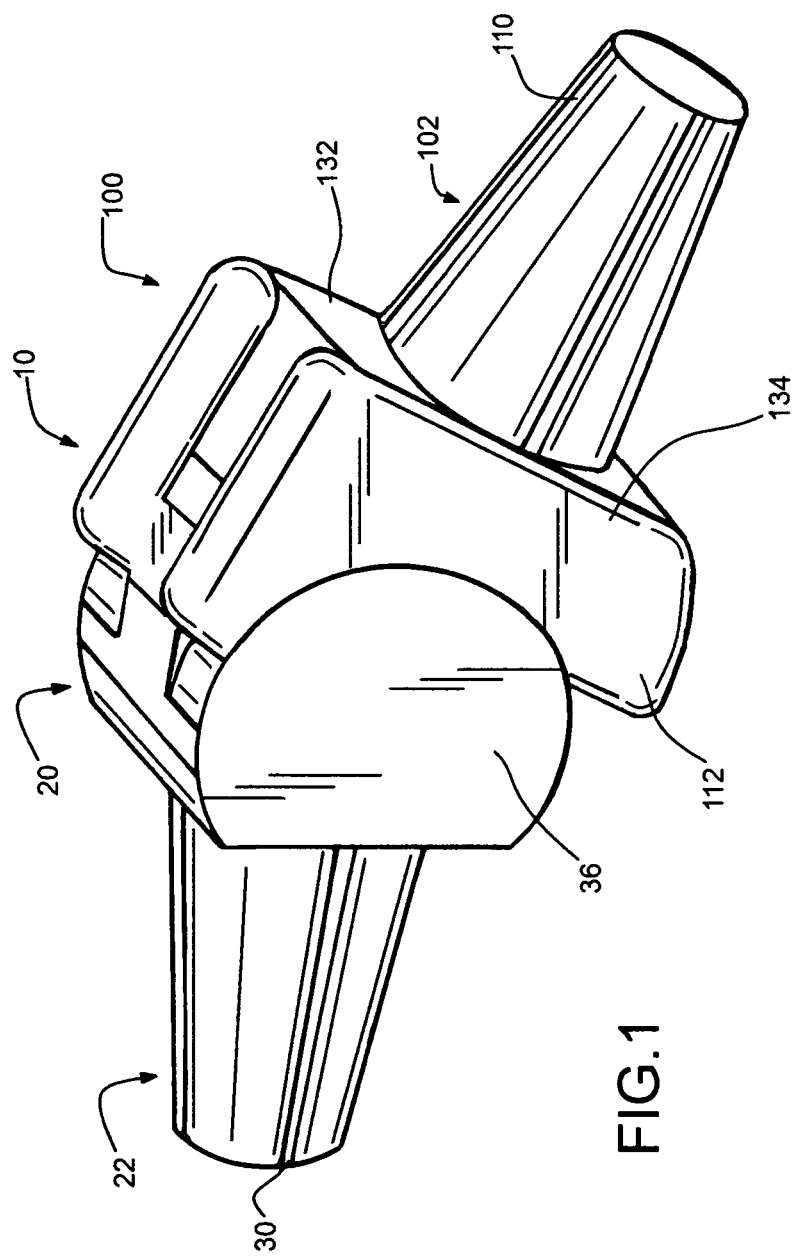
FIG. 1 is an isometric view of the prosthesis device of the present invention illustrating the male and female components of the device in a joined configuration.

Referring to FIG. 1, the present invention is for a metacarpal-phalangeal prosthetic replacement device 10 that replicates the various movements available in a human phalangeal or other joint. The prosthesis 10 includes two engaging components and which are further delineated herein as a male component 20 and a female component 100.

Referring with greater particularity to FIGS. 1-4, the male component 20 generally has an overall length, $L_2$, of from about 0.5 of an inch to about 4 inches, and preferably is from about 0.5 of an inch to about 1.2 inches. The male component 20 includes a substantially longitudinally centered, first conically shaped shank or tapered pylon 22. The pylon 22 having a relatively smaller diameter terminal portion 24 and a distal, relatively larger portion 26 that adjoins to a head portion 28. The conically shaped shank 22 is adapted to be inserted into the medullary canal of a bone after the end has been resected and a receiving void is created in the bone. The relatively smaller diameter terminal portion 24 has a radius, $R_0$, of from about 0.05 of an inch to about 0.8 of an inch, and preferably is from about 0.1 to about 0.5 of an inch. The conically shaped shank 22 has a length, $L_1$, of from about 0.15 to about 3.0 inches, preferably is from about 0.20 to about 2.0 inches and more preferably from about 0.25 to about 1.0 inch. The distal, relatively larger portion 26 of the conically shaped shank 22 has a radius of from about 0.1 of an inch to about 1.1 inches, and preferably is from about 0.1 of an inch to about 0.8 of an inch with the stipulation that the radius, $R_0$, is always less than the radius of the distal, relatively larger portion 26.

The conically shaped shank 22 includes a groove or channel 30 that can have a "V", "U" or any other configuration known to those skilled in the art. The channel 30 can have a depth of from about 0.1% to about 45% of the radius $R_0$, and preferably is from about 0.1% to about 0.25% of the radius $R_0$. In a preferred embodiment, the conically shaped shank 22 includes at least two channels 30 and more preferably at least 4 channels 30. The groove 30 can be substantially oriented along a longitudinal axis of the conically shaped shank 22. In an alternative embodiment, not shown, the channel(s) 30 can be circumferentially oriented, and more preferably have both a longitudinal and circumferential orientation along the distance from the relatively smaller portion 24 to the relatively larger portion 26. Although the smaller diameter terminal portion 24 is illustrated as having a blunt terminus, one skilled in the art will understand that the end can be rounded or include a means for increasing the terminus surface area, such as a "bow tie" or "fish bone" configuration.

The male head portion 28 is adjacent and fixedly attached to and positioned substantially at a right angle to the longitudinal axis of the relatively larger portion 26 of the first conically shaped shank 22. The male head portion 28 includes first and second condyles 32 and 34, respectively. Each condyle 32 and 34 has a lateral face 36 and first convex condylar surfaces 38 and 40, respectively. The first and second condyles 32 and 34 have a radius of curvature, $R_1$, of from about 0.05 of an inch to about 0.75 of an inch, preferably from about 0.1 to about 0.5 of an inch, and more preferably from about 0.1 to about 0.3 of an inch, as determined from the centerline of the lateral face 36.

Positioned between the first and second condyles 32 and 34 is an intercondylar extension 42 that projects outwardly relative to condyle surfaces 38 and 40. The intercondylar extension 42 has a second convex condylar surface 44 having a radius of curvature, $R_2$, that is substantially from about 0.01 to about 0.4 of an inch greater than radius of curvature $R_1$, preferably is from about 0.03 to about 0.25 of an inch greater than curvature $R_1$, and more preferably is from about 0.05 to about 0.20 of an inch greater than curvature $R_1$. The intercondylar extension 42 substantially follows the curvature of the condyles 32 and 34 convex shape and is adapted to engage a channel in the female head, described below. The intercondylar extension 42 is substantially longitudinally aligned relative to the convex surfaces 38 and 40 of the juxtaposed condyles 32 and 34.

Desirably, the male component 20 includes a slight planar surface 46 dorsally positioned that extends substantially from the beginning of convex condylar surface 38 and 40 to the beginning of the second convex condylar surface 44. This planar surface 46 interacts with a complementary and cooperative portion on the female component 100 and assists in retaining the extensor tendon during manipulation.

Figure 2:
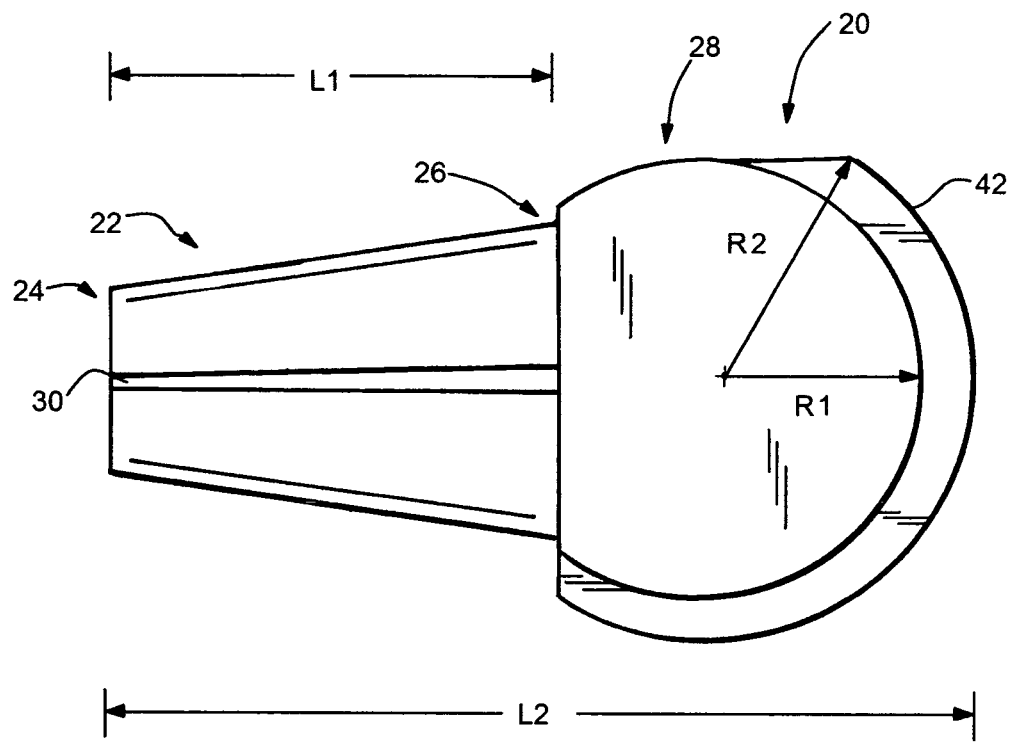
FIG. 2 is a side view of the male component of the prosthesis device.
Figure 4:
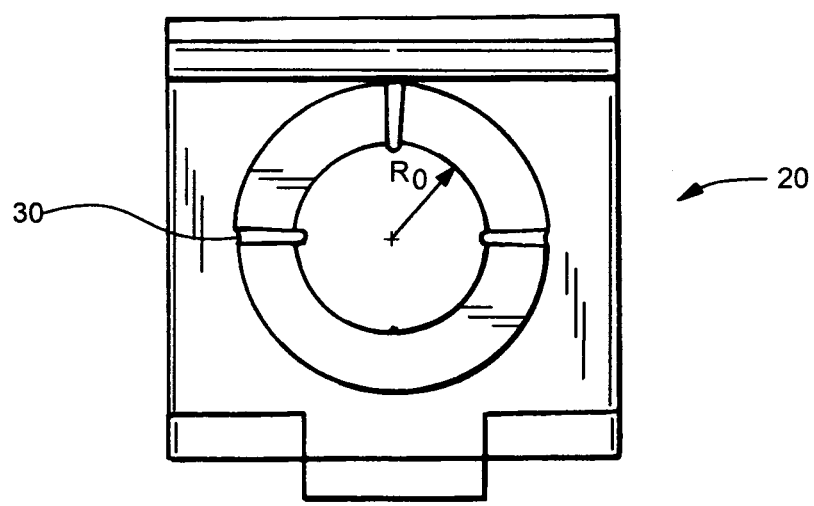
FIG. 4 is a front view of the male component of the prosthesis device.
Figure 3:
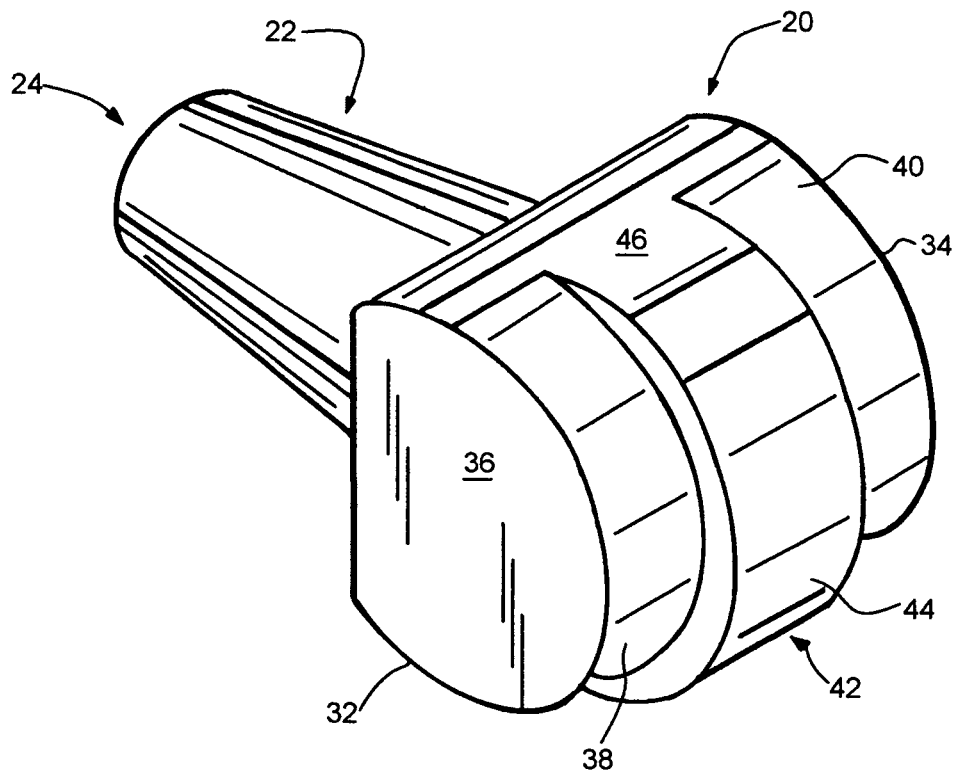
FIG. 3 is an isometric view of the male component of the prosthesis device.
Figure 7:
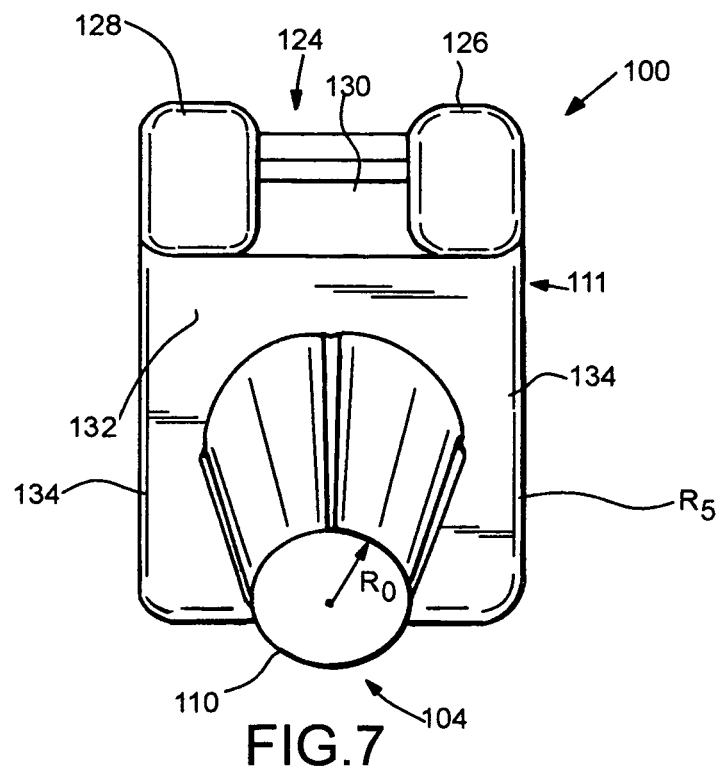
FIG. 7 is an isometric frontal view of the female component of the prosthesis device.
Figure 5:
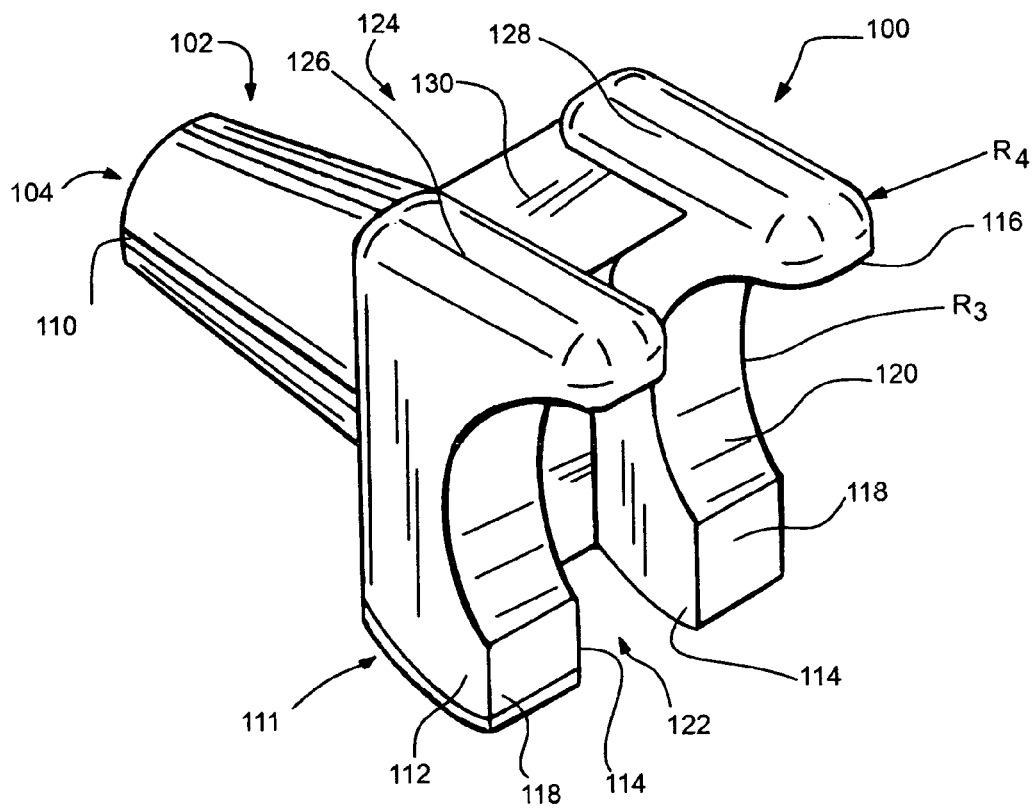
FIG. 5 is an isometric view of the female component of the prosthesis device.
Figure 6:
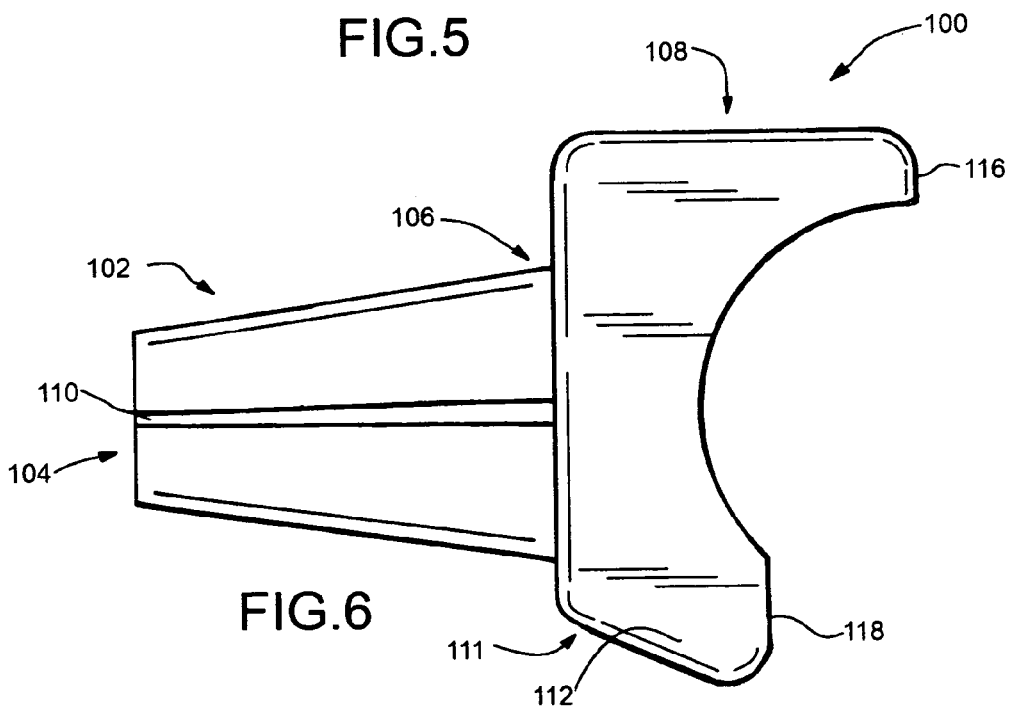
FIG. 6 is a side view of the female component of the prosthesis device.

Referring to FIGS. 2 and 4, the male head 28 can include a relaxed curvature at the edges where the relatively larger portion 26 of the conically shaped shank 22 joins with the male head portion 28. This curvature is optional and may have a considerably greater radius of curvature than shown so that sharp curves and edges are rounded.

Referring to FIGS. 1 and 5-7, parts are numbered as in FIGS. 1-4 insofar as possible. The metacarpal-phalangeal prosthetic replacement device 10 further includes a female component 100 adapted to engage with at least a portion of the male component 20. The female component 100 includes a substantially longitudinally centered, second conically shaped shank or tapered pylon 102 having a relatively smaller diameter terminal portion 104 and a distal, relatively larger portion 106. The relatively larger portion 106 adjoins to a head portion 108. The second conically shaped shank 102 is adapted to be inserted into the medullary canal of a bone after the end has been resected and an opening created. The relatively smaller diameter terminal portion 104 has a radius that desirably is similar to $R_0$, described above, i.e., of from about 0.05 of an inch to about 0.8 of an inch, and preferably is from about 0.1 to about 0.5 of an inch. The conically shaped shank 102 has a length similar to $L_1$, described above, i.e., of from about 0.15 to about 3.0 inches, preferably from about 0.20 to about 2.0 inches and more preferably from about 0.25 to about 1.0 inch. The distal, relatively larger portion 106 of the conically shaped shank 102 has a radius of from about 0.1 of an inch to about 1.1 inches, and preferably is from about 0.1 of an inch to about 0.8 of an inch with the stipulation that the radius, $R_0$, is always less than the radius of the distal, relatively larger portion 106.

The second conically shaped shank 102 includes a substantially longitudinally oriented groove or channel 110 that can have a "V", "U" or any other configuration known to those skilled in the art. The channel 110 can have a depth of from about 0.1% to about 45% of the radius $R_0$, and preferably is from about 0.1% to about 0.25% of the radius $R_0$. In a preferred embodiment, the conically shaped shank 102 includes at least two channels 110 and more preferably at least 4 channels 110. In an alternative embodiment, not shown, the channel(s) 110 can be circumferentially oriented, and more preferably have both a longitudinal and circumferential orientation along the distance from the relatively smaller portion 104 to the relatively larger portion 106. Although the smaller diameter terminal portion 104 is illustrated as having a blunt terminus, one skilled in the art will understand that the end can be rounded or include a means for increasing the terminus surface area, such as a "bow tie" or "fish bone" configuration.

The female head portion 108 is adjacent and permanently affixed to the relatively larger portion 106 of the conically shaped shank 102. The female head portion 108 includes two outer lateral side portions 111. Since lateral sides 111 are similar, only one will be described in detail unless otherwise noted. The lateral side portion 111 includes an outer lateral side 112, an inner lateral side 114, an upper portion 116 and a lower portion 118. Each lateral side portion 111 includes a concave recess 120 having a radius of concave curvature $R_3$ that is adapted to cooperatively engage with the convex condylar surface 38 of the male component, i.e., $R_1$ is substantially equal to $R_3$. Advantageously, the upper portion 116 partially overlays the first and second condyles of the male head portion 28 so as to prevent hyper or hypo extension of the joint.

The two lateral sides 111 define an intermediate concave condylar recess, slot or groove 122 that is adapted to cooperatively and rotationally engage the intercondylar extension 42 of the male component 20. The intermediate concave condylar recess 122 can have a radius of curvature substantially equal to $R_2$ with the noted understanding that the curvature of the intermediate concave condylar recess 122 is adapted engage to engage the second convex condylar surface 44. In one embodiment, the dimensions of the slot 122 are such that slight lateral rotation perpendicular to the direction of flexing may be possible. The inner lateral sides 114 defining the slot 122 may be slightly enlarged relative to the dimension of the intercondylar extension 42 to allow the intercondylar extension 42 to be loosely, but not sloppily, engaged in the slot 122. Alternatively, the edges of the intercondylar extension 42 may be externally chamfered, recessed, rounded or tapered slightly about of from about 0.1° to about 15°, and preferably from about 3° to about 8° so that slight rotational or sideways motion perpendicular to the flexure motion is possible. This allows the finger a limited universal movement more closely approximating the movement of a normal joint.

Positioned on the dorsal or top portion 124 of the female head 108 are first and second spaced-apart protuberances 126 and 128 that are continuations of the lateral side portions 111 and define a part of the upper portions 116. The protuberances 126 and 128 are substantially aligned along the longitudinal axis of the female head portion 100 and have a width substantially equal to the width of the concave recess 120. The first and second protuberances 126 and 128 define a median dorsal channel 130 that is the area proximate to the longitudinal protuberances 126 and 128. The median dorsal channel 130 in combination with the longitudinal protuberances 126 and 128 provide a pathway for the extensor tendon and advantageously, provide a means for limiting side movement of the tendon. The first and second protuberances 126 and 128 have a height, as measured from the median dorsal channel to the top of the protuberance, of from about 0.01 of an inch to about 0.75 of an inch. Preferably, the first and second protuberances 126 and 128 have a height of from about 0.05 of an inch to about 0.50 of an inch and more preferably have a height of from about 0.1 of an inch to about 0.25 of an inch.

Advantageously, the protuberances 126 and 128 extend above the dorsal plane to ensure the extensor tendon is retained adjacent to the prosthesis device. The face 132 of the head 108 includes sides 134 having a relaxed curvature, $R_5$, at the edges where the relatively larger portion 26 of the conically shaped shank 102 joins with the female head portion 108. This curvature is optional and may have a considerably greater radius of curvature than shown so that sharp curves and edges are rounded. Another advantage of the present invention is that the connection between the pylon and the joint itself are extrusions without any filleting or smoothing of contours.

The prosthetic device of the present invention can be made of materials compatible with the human body, such as, for example: metallic surgical materials such as, stainless steel, surgical cobalt-chrome alloy, titanium and titanium alloys, high purity alumina and more preferably a high purity alumina with at least 95% of theoretical density; ceramic materials; and suitable polymeric materials such as high density polyethylene, polycarbonate, polybutylterephthalate, and the like which may further include reinforcing components such as microfibers, glass beads, sintered metal, and the like. Alternatively, such metals and ceramics can be coated with one or more materials compatible with the human body to reduce wear along load bearing surfaces and provide a greater degree of fluidic movement of the device, such any one of the aforementioned metallic surgical materials coated with one or more of the aforementioned polymeric materials. Preferably, the present device comprises titanium, titanium alloys, high density polyethylene and combinations thereof.

The shank portions may be of square, rectangular, round, triangular or other convenient cross-section as is considered most convenient to the particular surgical problem. For example, a metacarpal having a somewhat rectangular medulla, a rectangular cross-section may be advantageous although fitting of round shapes may be easier in the phalanges. Likewise the head portions may be of generally cylindrical or spherical shape if desired or with an essentially rectangular outline as viewed from the end. In any case, it is usually desirable to provide a right-angled shoulder at the point where the conically shaped shank and head join so that surgical implantation will be simplified by requiring a right-angle cut at the end of the bone to align the joint correctly. The conically shaped shank portions 22 and 102 may advantageously provided with porous ceramic coating so that the shanks are susceptible to bone penetration and growth and thereby becoming thoroughly bonded in the medullary canals. Cementing may also be employed if desired. Postoperative measures are expectedly necessary to assure minimal resorption of bone and provide normal joint movement.

Surgical implantation of the present device requires dissection to reveal the joint and resection of the bones as necessary to fit the prosthesis. The extensor tendon is suitably held away from the site when the prosthesis is introduced. The extensor tendon is finally placed in the dorsal groove of the prosthesis followed by closing of the incision.

As can be seen from the above description, either the male component or female component may be inserted into the metacarpal body, but preferably, it is the male end that is secured and embedded within a cavity (not shown) provided in the metacarpal bone (not shown) and the female component affixed to the distal phalangeal bone. This arrangement allows for the extensor tendon to reside within the flat area 130 and allows the extensor tendon to apply a substantially longitudinally directed force retaining the male and female components in a joined configuration.

Having described the invention in detail, those skilled in the art will appreciate that modifications may be made to the various aspects of the invention without departing from the scope and spirit of the invention disclosed and described herein. It is, therefore, not intended that the scope of the invention be limited to the specific embodiments illustrated and described but rather it is intended that the scope of the present invention be determined by the appended claims and their equivalents. Moreover, all patents, patent applications, publications, and literature references presented herein are incorporated by reference in their entirety for any disclosure pertinent to the practice of this invention.

What is claimed is:

1. A surgically implantable metacarpal-phalangeal prosthetic replacement device comprising:
   a. a male component comprising:
      i. a first conically shaped shank adapted to be inserted into a medullary canal of a bone; and
      ii. a male head portion connected to said first conically shaped shank, said male head portion having two spaced-apart lateral condyles with convex condylar surfaces having a circular arc of greater than 180° around a center of curvature, and an intercondylar portion positioned between said spaced-apart lateral condyles extending outwardly relative to the convex condylar surfaces; and
   b. a female component comprising:
      iii. a second conically shaped shank adapted to be inserted into a medullary canal of a bone; and
      iv. a female head portion connected to said second conically shaped shank, said female head portion include spaced-apart lateral side portions having concave recessed load-bearing surfaces that are complementary to and engage said convex condylar surfaces of the male component, said lateral sides further defining an intermediate concave condylar recess that engages said outwardly extending intercondylar portion of the male component, said female head portion further comprising dorsal or upper first and second protuberances which define a channel portion that is adapted to receive an extensor tendon.

2. The prosthetic replacement device of claim 1 wherein at least one of said first and second conically shaped shanks includes a groove.

3. The prosthetic replacement device of claim 2 wherein said groove is substantially aligned along a longitudinal axis of said at least one of said first and second conically shaped shank. pg,18

4. The prosthetic replacement device of claim 1 wherein said male head portion is connected to said first conically shaped shank at a substantially right angle.

5. The prosthetic replacement device of claim 1 wherein said convex condylar surfaces have a radius of curvature, $R_1$ of from 0.05 of an inch to 0.75 of an inch.

6. The prosthetic replacement device of claim 5 wherein said convex condylar surfaces have a radius of curvature of from 0.1 to 0.5 of an inch.

7. The prosthetic replacement device of claim 5 wherein said intercondylar portion has a second convex condylar surface having a radius of curvature, $R_2$, that is from 0.01 to 0.4 of an inch greater than radius of curvature $R_1$.

8. The prosthetic replacement device of claim 7 wherein said intercondylar portion has a radius of curvature that is from 0.03 to 0.25 of an inch greater than curvature $R_1$.

9. The prostetic replacement device of claim 7 wherein said intercondylar portion has a radius of curvature that is from 0.05 to 0.20 of an inch greater than curvature $R_1$.

10. The prosthetic replacement device of claim 7 wherein said intermediate concave condylar recess has a radius of curvature substantially equal to $R_2$ so that said intermediate concave condylar recess is a mirror image to said second convex condylar surface.

11. The prosthetic replacement device of claim 1 wherein said concave recessed load-bearing surfaces have a radius of concave curvature $R_3$ that is adapted to cooperatively engage with the convex condylar surface of said male component.

* * * * *